(12) United States Patent
Bonutti

(10) Patent No.: US 7,497,864 B2
(45) Date of Patent: Mar. 3, 2009

(54) TISSUE FASTENER AND METHODS FOR USING SAME

(75) Inventor: Peter M. Bonutti, Effingham, IL (US)

(73) Assignee: Marctec, LLC., Effingham, IL (US)

( * ) Notice: Subject to any disclaimer, the term of this patent is extended or adjusted under 35 U.S.C. 154(b) by 565 days.

(21) Appl. No.: 10/427,151

(22) Filed: Apr. 30, 2003

(65) Prior Publication Data

US 2004/0220591 A1 Nov. 4, 2004

(51) Int. Cl.
*A61B 17/10* (2006.01)
(52) U.S. Cl. .................................... 606/139
(58) Field of Classification Search ........... None
See application file for complete search history.

(56) References Cited

U.S. PATENT DOCUMENTS

| | | | | |
|---|---|---|---|---|
| 2,811,154 A | * | 10/1957 | Scholl | 602/77 |
| 4,428,101 A | * | 1/1984 | Harkavy | 24/712.4 |
| 5,171,253 A | * | 12/1992 | Klieman | 606/158 |
| 5,254,113 A | | 10/1993 | Wilk | |
| 5,290,217 A | * | 3/1994 | Campos | 600/37 |
| 5,324,294 A | * | 6/1994 | Elia et al. | 606/76 |
| 5,361,780 A | * | 11/1994 | Kellan | 128/849 |
| 5,503,908 A | * | 4/1996 | Faass | 428/198 |
| 5,906,617 A | * | 5/1999 | Meislin | 606/72 |
| 5,909,617 A | | 6/1999 | Manning et al. | |
| 6,031,148 A | * | 2/2000 | Hayes et al. | 623/11.11 |
| 6,042,534 A | * | 3/2000 | Gellman et al. | 600/30 |
| 6,083,244 A | * | 7/2000 | Lubbers et al. | 606/232 |
| 6,319,264 B1 | * | 11/2001 | Tormala et al. | 606/151 |
| 6,365,149 B2 | * | 4/2002 | Vyakarnam et al. | 424/93.1 |
| 6,599,310 B2 | * | 7/2003 | Leung et al. | 606/228 |
| 6,986,771 B2 | * | 1/2006 | Paul et al. | 606/61 |
| 6,991,643 B2 | * | 1/2006 | Saadat | 606/221 |
| 2003/0064358 A1 | * | 4/2003 | Elson et al. | 435/4 |
| 2003/0236575 A1 | * | 12/2003 | Yu et al. | 623/32 |

* cited by examiner

*Primary Examiner*—Todd E Manahan
*Assistant Examiner*—Tuan V Nguyen
(74) *Attorney, Agent, or Firm*—Fleit Gibbons Gutman Bongini & Bianco; Paul D. Bianco; Martin Fleit

(57) ABSTRACT

In one embodiment, a hook fastener has a plurality of hooks and a loop fastener has a plurality of loops to secure tissues sections to one another. At least one of these fasteners has a porous surface to allow tissue ingrowth to secure the fastener to the tissue. In another embodiment, only a single fastener is used, with a section of tissue being treated to engage and mate with the fastener. The disclosed tissue fastening systems can be used for a number of applications. One such example includes fastening tissue sections by wrapping a tissue fastener around the tissue and securing the fastener on itself. A suture may also be secured with the tissue fastener.

7 Claims, 4 Drawing Sheets

TISSUE FASTENER AND METHODS FOR USING SAME

FIELD OF THE INVENTION

The present invention relates generally to a tissue fastener and in particular to a hook and loop type fastener with provisions to allow tissue ingrowth. The present invention also relates to a wide variety of methods of using the fastener for surgical and other interventional procedures.

BACKGROUND OF THE INVENTION

The vast majority of surgical procedures require suturing or otherwise coupling first and second tissue sections. This coupling process can be difficult to accurately perform and/or time consuming, particularly if a laparoscopic or other minimally invasive approach is used. Given this need, the prior art teaches a wide variety of fasteners. Although some of these fasteners have been specifically designed for medical applications, a number of fasteners were developed for non-medical applications and modified for biological uses.

One such fastener that can be used for different applications is the so-called hook and loop type fastener. Hook and loop fasteners have found use in a wide variety of fields, including surgical procedures. For example, U.S. Pat. No. 5,906,617 to Meislin discloses surgical repair with a hook and loop type fastener. The '617 patent teaches first and second sheets that are fixed to tissue with fibrin glue, either alone or in association with sutures and/or staples. Although this type of fixation is suitable for initial and short term stability, the use of sheets in combination with glue makes no provision for long term biologic fixation, i.e. integration of the sheets with the tissue. Furthermore, the requirement of two glued sheets for all applications also limits the utility to some surgical procedures.

U.S. Pat. No. 5,254,113 to Wilk discloses a method for use of a strip of a biocompatible material in performing an anastomosis. The method disclosed includes juxtapositioning free ends of two sections of a resected tubular organ so as to form a continuous lumen through the sections, placing a strip of biocompatible material over the sections at the seam and bonding the strip to the outer surfaces of the sections so as to form a seal about the sections at the seam. An inflatable balloon is used to maintain the sections in position and can be absorbed by the body or excreted. The sections may also be stapled or sutured along the seam prior to the sealing of the strip over the seam, or the seam could be laser welded or sealed with a biocompatible adhesive. However, the use of a balloon, laser welding, or other seals may be prohibited by the size, location, or part of the body that may need to be sealed.

Thus, the need exists for an improved tissue fastening system. Additional features and advantages of the invention will be set forth in the description that follows, and in part will be apparent from the description, or may be learned by practice of the invention. The objectives and other advantages of the invention will be realized and attained by the apparatus and process particularly pointed out in the written description and claims, as well as the appended drawings.

SUMMARY OF THE INVENTION

The invention is directed to a tissue fastening system for coupling first and second tissue sections. The system includes a hook fastener having a tissue contacting portion for contacting the first tissue section and a fastening portion with a plurality of hooks, and a loop fastener having a tissue contacting portion for contacting the second tissue section and a fastening portion with a plurality of loops, wherein the plurality of hooks engage the plurality of loops to couple the first and second tissue sections and wherein at least a portion of one of the hook fastener tissue contacting portion and the loop fastener tissue contacting portion has a porous surface allowing tissue ingrowth to thereby secure the fastener to tissue.

In another aspect, the invention is directed to a tissue fastening system for coupling first and second tissue sections that includes a tissue contacting portion for contacting the first tissue section, and a fastening portion having at least one of a plurality of hooks and a plurality of loops, the fastening portion being integral with the tissue contacting portion and wherein the at least one of the plurality of hooks and plurality of loops engages the second tissue section to thereby couple the first and second tissue sections.

In yet another aspect of the invention, a method of coupling first and second tissue sections includes treating a portion of the first tissue section to have a surface with one of a plurality of hooks and a plurality of loops, attaching a fastener to the second tissue section, the fastener having a fastening portion with the other of a plurality of hooks and a plurality of loops, and placing the fastening portion in contact with the surface of the first tissue section to thereby couple the first and second tissue sections.

In another aspect of the present invention, a tissue fastening method is disclosed for coupling first and second tissue sections, the method includes bringing the first tissue section and the second tissue section into contact with one another, wrapping a fastener around a portion of the first and second tissue sections, and securing the fastener on itself to maintain the first and second tissue sections in contact with one another, wherein the fastener has a porous surface allowing tissue ingrowth to thereby secure the fastener to the first and second tissue sections.

In another aspect of the invention, a tissue fastening system for coupling first and second tissue sections is disclosed that includes a suture engaging the first and second tissue sections to maintain the first and second tissue sections in a predetermined relationship, a hook fastener having a plurality of hooks, and a loop fastener having a plurality of loops, wherein the plurality of hooks engage the plurality of loops with a portion of the suture therebetween to thereby secure the suture relative to the first and second tissue sections.

It should be understood that the present invention has a plurality of different features which may be utilized separately or in various combinations. It is also contemplated that the various features of the invention may be utilized with known features from the prior art. Although specific combinations of features have been described herein, it is contemplated that other combinations of features will be apparent to those skilled in the art and will be formed.

BRIEF DESCRIPTION OF THE DRAWINGS

The foregoing and other features of the present invention will become apparent to one skilled in the art upon a consideration of the following description of the invention with reference to the accompanying drawings, wherein.

DETAIL DESCRIPTION OF THE INVENTION

Figure 1:
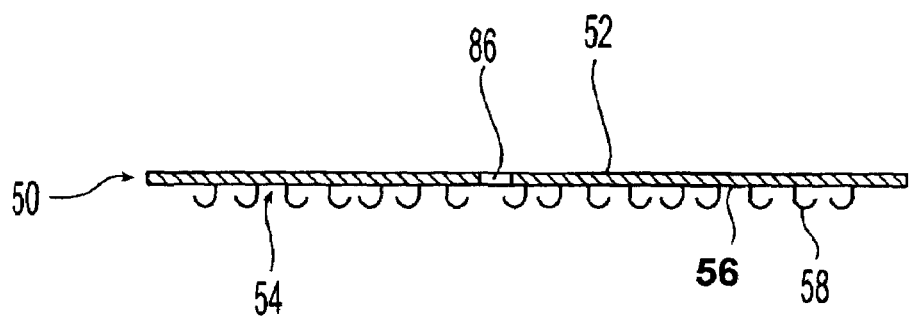
FIG. 1 shows a schematic representation of a cross section of one embodiment of a fastener according to the present invention in which the fastener has a plurality of hooks on a surface.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto. Finally, any reference to a particular biological application, such as use for anastomosis applications, is simply used for convenience as one example of a possible use for the invention and is not intended to limit the scope of the present invention thereto.

FIG. 1 shows a tissue fastener 50 according to the present invention. Fastener 50 includes a tissue contacting portion 52 and a fastening portion 54. In use, tissue contacting portion 52 contacts the tissue and preferably has a porous surface 56 having a plurality of interstitial spaces allowing tissue ingrowth by the tissue on which it is placed, thereby securing fastener 50 to the tissue. Porous surface 56 may comprise all or only a portion of the tissue contacting portion 52 of fastener 50. The porous surface 56 provide long term stability with the biologic integration of fastener 50 to the tissue.

Fastening portion 54 has a plurality of hooks 58 on a surface. Hooks 58 are similar to the hooks found on a hook and loop type fastener. One example of such a hook and loop type fastener is commercially available under the trademark VELCRO®. In use, hooks 58 engage loops or other similarly textured surface so that fastener 50 is secured to whatever the hooks 58 engage.

Figure 2:
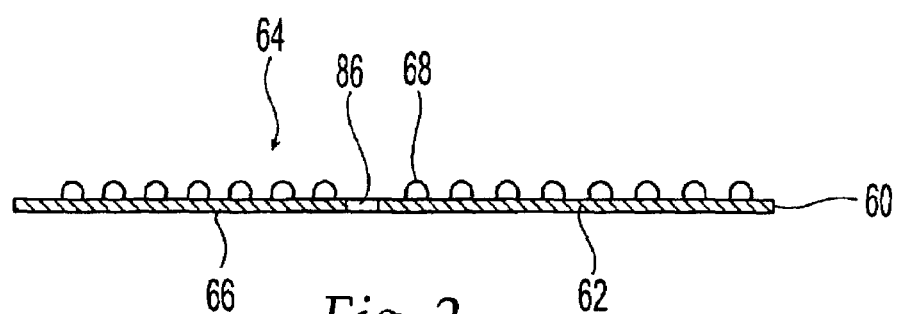
FIG. 2 shows a schematic representation of a cross section of one embodiment of a fastener according to the present invention in which the fastener has a plurality of loops on a surface.

FIG. 2 shows a tissue fastener 60 that can be used with fastener 50 or by itself. Fastener 60 includes a tissue contacting portion 62 and a fastening portion 64. In use, tissue contacting portion 62 contacts the tissue and has a porous surface 66 having a plurality of interstitial spaces allowing tissue ingrowth by the tissue on which it is placed, thereby securing fastener 60 to the tissue. As with fastener 50, all or only a portion of the tissue contacting portion 62 may have the porous surface 66. The porous surface 66 of tissue contacting portion 62 provides long term stability with biologic integration of fastener 60 to the tissue.

Fastening portion 64 is provided with a plurality of loops 68 on a surface. Loops 68 are similar to the loops found on a hook and loop type fastener (again, the most widely recognized example being commercially available under the trademark VELCRO®), but may be any structure that allows for a hook-like structure to engage the loops 68. The loops 68 may either be of the monofilament or multifilament type.

Fasteners 50 and 60 can be made of any biocompatible material. Although commercially available hook and loop fasteners are generally not useful in the present invention, the same techniques used in manufacturing commercial hook and loop fasteners can be used to manufacture fasteners of this type of materials that are biocompatible. In one embodiment, fastener 50 (and/or fastener 60) is made from a non-biodegradable material and is intended to remain in the patient indefinitely. These materials include metals and their alloys, polymers, ceramics, and composite material. For example DACRON® polyester is widely used as suture material and in implantable surgical devices. Polycarbonates are also generally compatible with biological tissue. These and other polymeric materials can be formed into hook and loop fastener components using standard manufacturing methods.

In another embodiment, at least a part of the fasteners 50, 60 is made of a biodegradable material that, with time, is absorbed and assimilated by the body after the tissue regenerates. Suitable biodegradable materials that can be manufactured or formed as hook and loop fasteners include polylactic acid, polycaprolactone, polyglycolic acid, polyanhydrides (e.g. polyterephthalic acid/sebaic acid anhydride, polydioxanone), polyamino acids (e.g. polyglycine, etc.), and copolymers of lactic acid with comonomeric materials such as glycolic acid, hexamethyl sebacic acid, etc. These combine the qualities of non-immunogenicity, non-toxicity and an acceptable rate of bioabsorption versus regeneration of tissue.

Collagen and other polymers of biological origin (such as alginates, starch, etc.) are also suitable and can be treated to reduce the immunogenic potential. Modified natural polymers such as gelatin, oxidized cellulose, etc., may also be utilized. Hydroxyapatite coral may also be used. In one embodiment, at least a portion (e.g. the tissue contacting portion 52 and/or tissue contacting portion 62) of at least one of the fasteners 50, 60, is made using a scaffold material that can include viable cells. The scaffold material may be formed in many different ways. Some of the different methods are disclosed in co-pending Provisional Patent Application No. 60/387,013, filed Jun. 7, 2002 and entitled "Implanting Cells", the contents of which are incorporated herein by reference. One way in which the scaffold may be formed is by removing an organ or a portion of an organ from a body, either the patient's own body or another body. Cells and/or other tissue may be removed from the organ or portion of an organ to leave a collagen matrix support structure having a configuration corresponding to the configuration of the organ or portion of an organ. Viable cells are positioned on the collagen matrix support structure. The scaffold, which has a configuration corresponding to the configuration of an organ or portion of an organ, is positioned in the patient's body with the viable cells disposed on the support structure.

It is contemplated that the scaffold may have a composite construction and be formed of different materials which have different characteristics. It is also contemplated that the viable cells may be any desired type of viable cells. The viable cells may correspond to cells which were in a damaged organ or other portion of a patient's body. More than one type of viable cell may be positioned on the same support structure. The support structure and viable cells may be positioned in either hard or soft tissue.

Regardless of the material used to fabricate the fasteners, additives may be incorporated in the fasteners 50, 60. Such additives may include materials such as plasticizers, citrate esters, hexametholsebacate, antibiotics (e.g., tetracyclines, penicillins, mefronidazole, clindamycin, etc.), to prevent infection, etc., or to accomplish other desired conditions or results, including for example, tissue inductive growth factors to promote a growth of tissue between the porous surface 66. Addition additives or therapeutic agents include osteoinductive, biocidal, or anti-infection substances. Suitable osteoinductive substances include, for example, growth factors. The growth factors may be selected from the group of IGF (insulin-like growth factors), TGF (transforming growth factors), FGB (fibroblast growth factors), EGF (epidermal growth factors), BMP (bone morphogenic proteins), and PDGF (platelet-derived growth factors).

Further, these devices can be formed, in part, in situ, using fast drying adhesives such as fibrin glue which attach the fastener to the bone or other tissue and also attach the hooks or loops to the bone or tissue. Another important feature of this invention is that sterile hook and loop material may be provided in larger sheets or rolls and cut at the operating table into the exact size and shape needed to obtain the best attachment.

Figure 3:
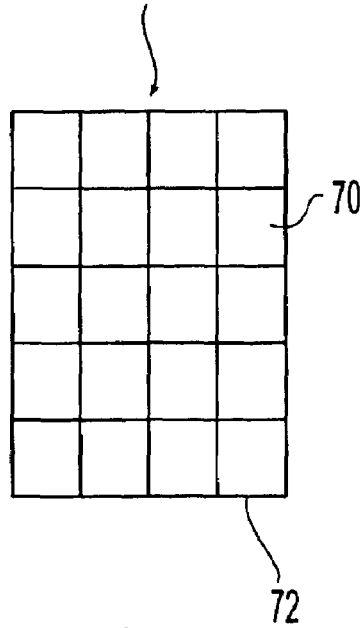
FIG. 3 shows a top view of one embodiment of a tissue contacting surface that can be used with fasteners according to the present invention.
Figure 4:
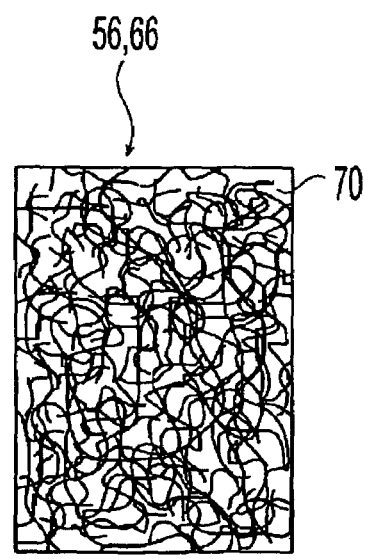
FIG. 4 shows a top view of another embodiment of another embodiment of a tissue contacting surface that can be used with fasteners according to the present invention.

As shown in FIGS. 3 and 4, porous surface 56, 66 has a plurality of interstitial or void spaces 70 that are sized to aid tissue ingrowth. As the tissue grows into and through the void spaces, fastener 50 and/or fastener 60 becomes biologically bonded to the tissue. Such bonding provides long term fixation superior to the long term fixation achievable with other means, such as suturing, stapling, gluing, and the like. In FIG. 3, the void spaces 70 are defined by a mesh 72. As shown, mesh 72 is formed so that each of void spaces 70 is approximately equal in size. However, mesh 72 can be formed so that void spaces 70 vary in size. For example, the void spaces 70 may all have the same length (top to bottom in the figure), but have varying widths (side to side in the figure), or vice versa. Also, the void spaces 70 may all have varying sizes, however slight. Also, as shown in FIG. 4, void spaces 70 may also be formed by randomly oriented filaments, causing the void spaces 70 to vary in size. As is well known in the art, porous surfaces 56 and 66 can be created by other means. For example, a porous beaded surface could be used for porous surfaces 56 and 66.

Regardless of their configuration and how they are formed, void spaces 70 are preferably sized to provide optimal tissue ingrowth depending on the tissue type. Typically, void spaces 70 range for bone from around 0.1 microns to 1000 microns. For bone tissue, suitable void spaces 70 range from about 8-10 microns or larger, preferably larger than about 20 microns and less preferably of about 250 microns or larger. Tissue ingrowth results in a stable implant of the fasteners 50 and 60, which is unlikely to allow them to migrate from the site of original implantation.

While both fasteners 50 and 60 are illustrated as having a porous surface, only one of fasteners 50 and 60 needs to be provided with a porous surface, if suitable for a particular application. One example of a fastening system that utilizes both fasteners 50 and 60 will now be discussed. However, as discuss below, fasteners 50 and 60 can be used independent of each other.

Figure 5:
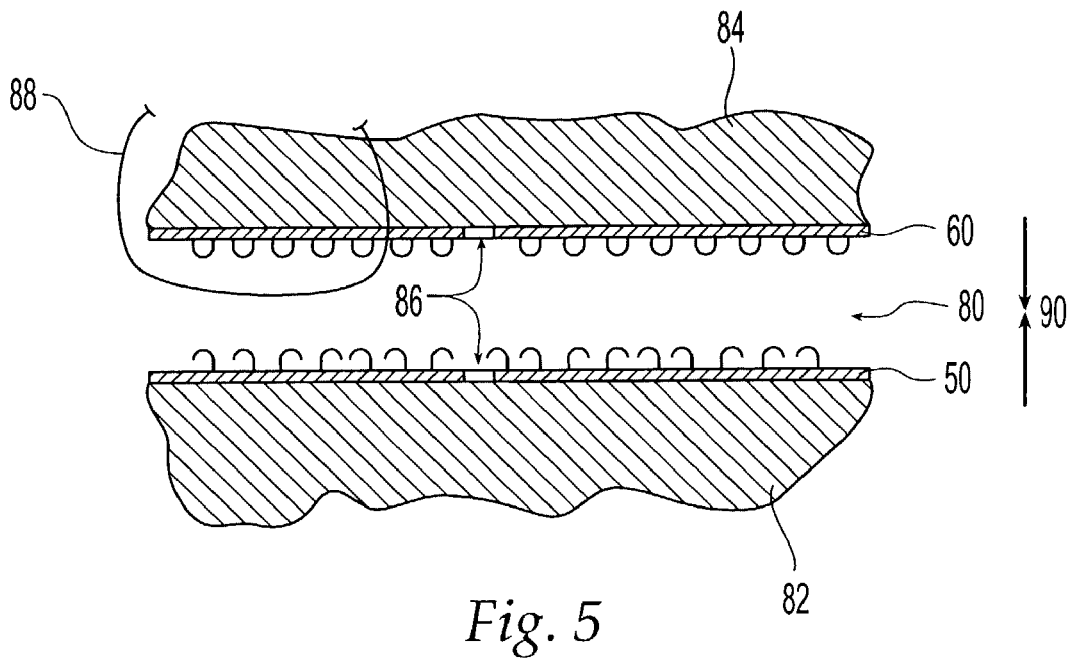
FIG. 5 shows a cross sectional view of the fastener of FIG. 1 in use with the fastener of FIG. 2 to secure two tissue sections together.

Fasteners 50 and 60, as illustrated in FIG. 5, can be placed on opposite sides of an opening 80 in tissue 82, 84. Although fastener 50 is shown on tissue section 82 and fastener 60 is shown on tissue section 84, they may be reversed. The fasteners 50, 60 can be attached to the tissue sections 82, 84 in a number of ways. For example, the fasteners may be attached simply by using surface tension of the two materials or by using a biocompatible glue to secure the fasteners in place to allow the tissue ingrowth if desired. It should be noted that while tissue sections 82, 84 are schematically illustrated in FIG. 5 to both be of the same or similar tissue types, either or both may have a different composition. For example, one of the tissue sections may be a bone and the other tissue section may be a tendon associated with a muscle to be reattached to the bone. As illustrated in FIG. 5, the fasteners may also have an anchoring hole 86, through which an anchoring member 88, such as suture, a staple or rivet, may be inserted to hold the fasteners in place. If, as noted above, the fasteners are biodegradable, then the anchoring member 88 can also be biodegradable so that it does not remain after the fasteners resorb.

Once the fasteners 50, 60 are in place on tissue sections 82, 84 then the tissue sections are pushed in the direction of arrows 90 to allow the fastening portions 54, 64 to engage one another to maintain the tissues portions in a relative location with respect to one another.

Rather than using both fasteners 50, 60, only one of the fasteners may be used. For example, if the fastener 50 is used and attached to tissue section 82, the hooks 58 may directly engage the tissue section 84. The fastener 50 may be attached to tissue section 82 in any manner discussed above, i.e., fibrin glue, anchoring member, etc. Prior to pressing the two tissues sections together, the tissue section 84 may also first be prepared to receive the hooks 58 to allow for a better engagement of the fastener 50 with the tissue section 84. For example, the tissue section may first be roughened with a rasp or other tool to provide the tissue section 84 with a surface that engages the fastener 50. Using a rasp, the tissue surface is broken up sufficiently to allow the hooks 58 to engage the tissue section 84. Other methods of preparing the surface of tissue section 84 are also contemplated. For example, hooks may be directly attached the surface, i.e., providing several sutures or other loops for the hooks 58 to engage.

Similarly, only the fastener 60 may be used with tissue section 84. The fastener 60 may be attached to tissue section 84 in any method as noted above. In order to allow the two tissue sections to be attached to one another, tissue section 82 may also be roughened with a rasp to provide the tissue with projections and elements on the tissue section 82 that engage the loops 68 on fastener 60.

Figure 8:
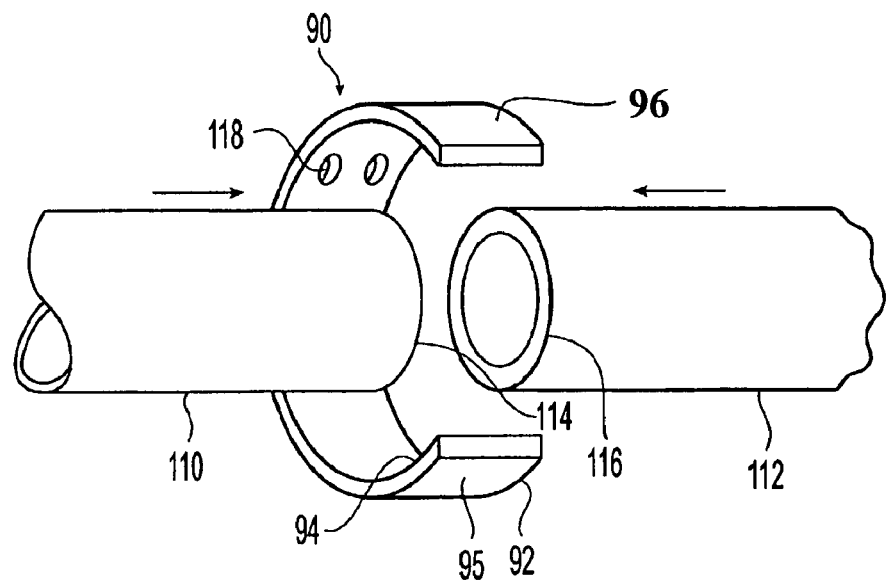
FIG. 8 shows the tissue fastening system of FIGS. 6 and 7 as it is applied to the tissue sections.

One example of an application in which only one of fasteners 50, 60 need be used is an anastomosis procedure, in which the ends of two vessels are connected (see FIG. 8). In such a situation, the ends of the vessels would be pre-treated as described above so that the ends engage either the hooks or loops, depending on the fastener that is used.

Figure 6:
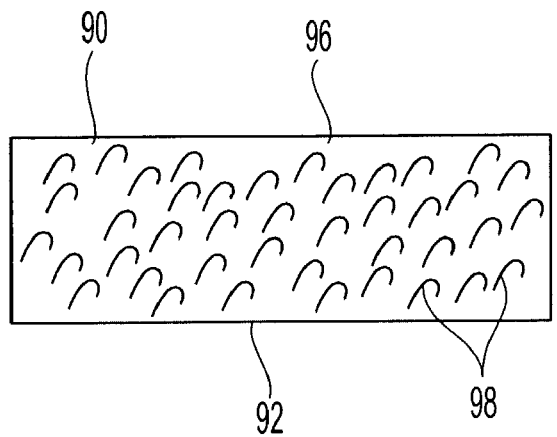
FIG. 6 shows a top view of another embodiment of a tissue fastening system that can be secured to itself according to the present invention.
Figure 7:
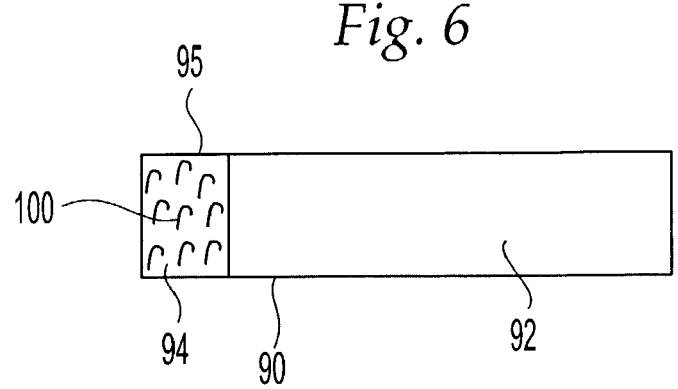
FIG. 7 shows a bottom view of the tissue fastening system of FIG. 6.

FIGS. 6-8 shows another embodiment of a tissue fastener that can be used to bring the ends of two tissues together. Fastener 90 has a tissue contacting portion 92 and a fastening portion 94. The fastening portion 94 is preferably at one end 95 of the fastener. This embodiment is similar to those discussed above in that it is of the hook and loop type and is made of biocompatible materials, and may even be made of biodegradable materials. Similarly, it may also have the mentioned additives to assist in healing the tissues into which it comes into contact. The tissue contacting portion 92 can have a porous surface 96 that is similar to the porous surface 54, and also has a plurality of interstitial spaces allowing tissue ingrowth and thereby securing fastener 90 to tissue. The tissue contacting portion 92 may also have a plurality of loops 98 to engage a plurality of hooks 100 on the fastening portion 94. It should be noted that the arrangement of loops and hooks can be reversed if desired.

As illustrated in FIG. 8, the fastener 90 is used to couple first 110 and second 112 tissue sections to one another. The first tissue section 110 and the second tissue section 112 are brought into contact with one another (or in close proximity)

along surfaces 114 and 116, respectively. Fastener 90 is then wrapped around a portion of each of the tissue sections, with the fastening portion 94 on the end overlapping the fastener 90 and engaging the tissue contacting portion 92 to secure the fastener to the tissue. The amount of overlap of the fastener 90 will depend on the type and size of the tissues being secured to one another. Also, while the fastener 90 is illustrated as having a rectangular shape, it should be noted that the fastener 90 could have any shape, including, for example, square, round, oval, or any other shape that would allow it to be used in the above described manner. Additionally, sterile hook and loop material can be cut not only to form the attachment per se but in lengths and/or widths to provide reinforcement for weakened tissue or bone.

Additionally, FIG. 8 illustrates the use of a fastener 90 on two tubular structures, but fastener 90 could also be used to bring the ends of two solid, or even partially solid tissues, together. Fastener 90 may also have anchoring holes 118 for an additional means by which to secure the fastener 90 to the tissues. The anchoring member to be used with the anchoring holes 118 should be consistent with the use of the fastener 90. As an alternative, or in conjunction with the anchoring member, fastener 90 can be heated to secure fastener 90 to the tissue. The heating would be done at a temperature that minimizes tissue necrosis, yet still allows some flow of the material of fastener 90 so that a seal is created between the tissue and fastener.

Figure 9:
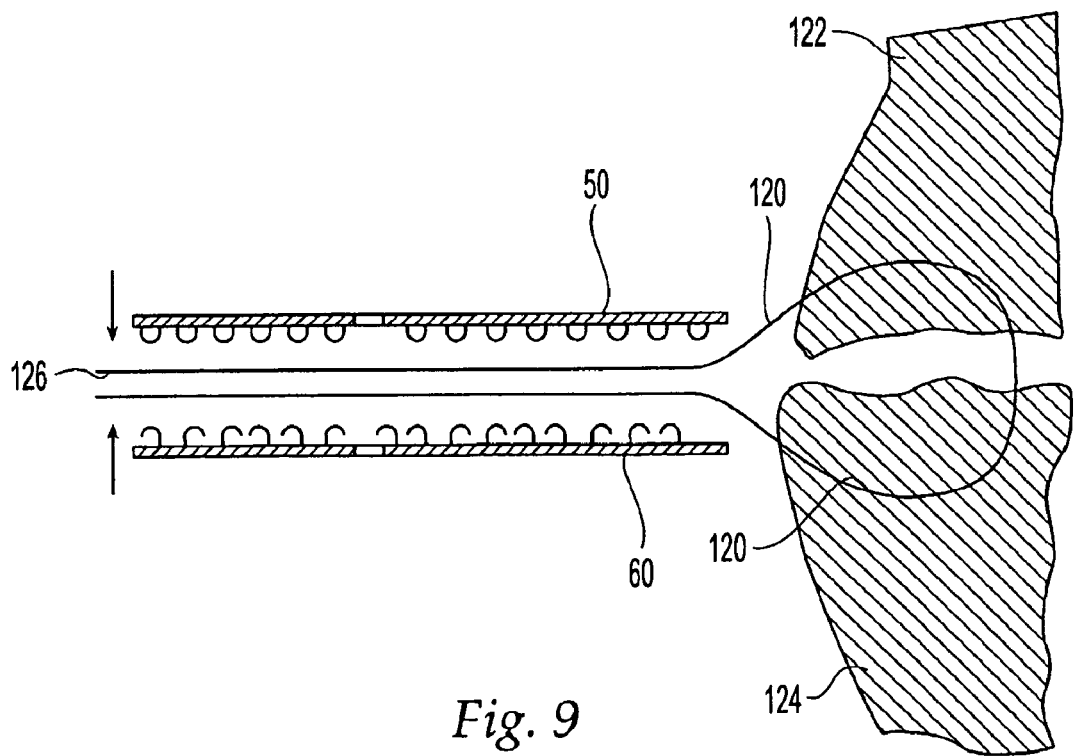
FIG. 9 shows a cross sectional view of the fastener of FIG. 1 in use with the fastener of FIG. 2 to lock a suture therebetween.
Figure 10:
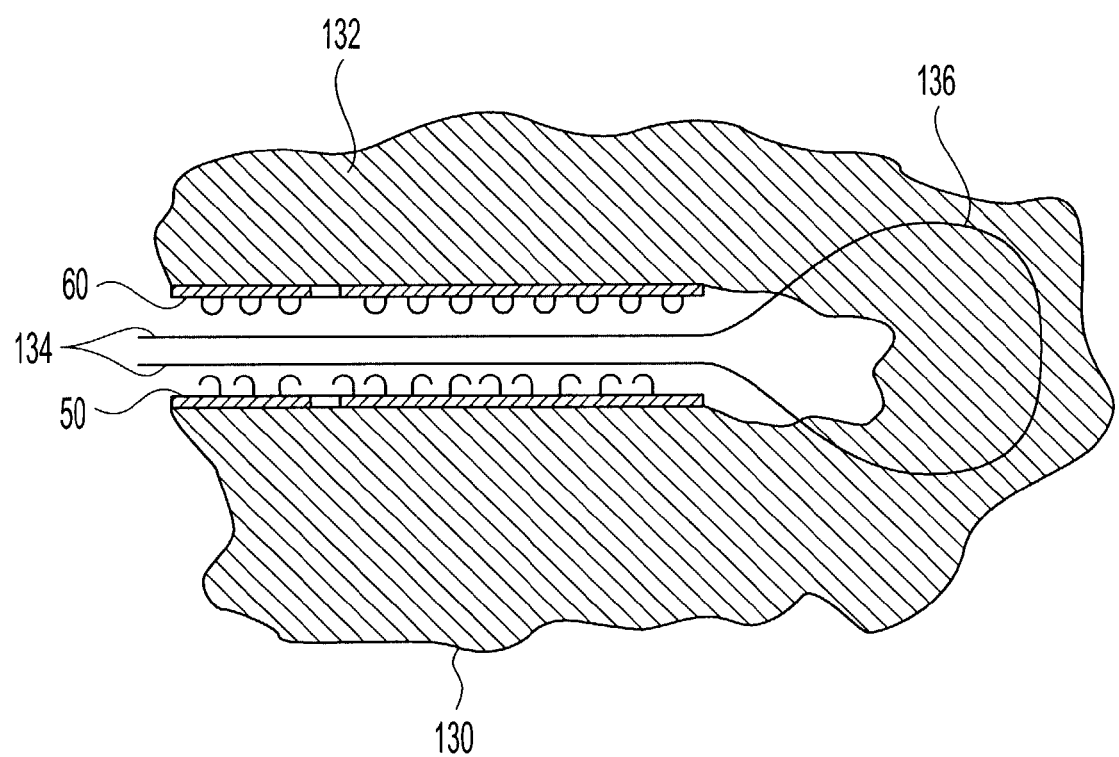
FIG. 10 shows a cross sectional view of the fastener to FIG. 1 in use with the fastener of FIG. 2 to lock a suture therebetween as well as the tissue sections.

Another use of a tissue fastener according to the present invention is illustrated in FIGS. 9 & 10. In one embodiment illustrated in FIG. 9, the fasteners 50 and 60 are used to secure the ends of a suture 120 outside of the tissue sections. The suture 120 is used to secure two tissue sections 122, 124 and the ends 126 of the suture 120 are then secured between fasteners 50 and 60 rather than tied off, as usually done. As with the previous embodiments, the hooks and loops engage one another, but in this embodiment the ends of the suture are disposed therebetween outside the tissue.

In FIG. 10, however, the fasteners 50 and 60 are at least partially disposed between the two tissue sections 130 and 132. The fasteners 50 and 60 secure not only the tissue sections as noted above, but they also secure the ends 134 of the suture 136. In this embodiment, the suture is typically internal and the use of fasteners 50 and 60 allow fewer sutures to be used since additional sutures are not needed to join the tissue sections 130 and 132 at the edge of the tissue. The fasteners 50 and 60, and the suture 136, are preferably also made from a biocompatible material, and most preferably from a biodegradable material. It should also be noted that the loop portion of the fastener 60 are preferably multifilament loops, to provide a stronger grip and to ensure that the ends 134 of the suture 136 are appropriately captured.

While various descriptions of the present invention are described above, it should be understood that the various features could be used singly or in any combination thereof. Therefore, this invention is not to be limited to only the specifically exemplary embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A tissue fastening system for coupling first and second tissue sections, the system comprising:
   a hook fastener having a tissue contacting side for contacting the first tissue section and a fastening side, positioned opposite said hook fastener tissue contacting side, with a plurality of hooks;
   a loop fastener having a tissue contacting side for contacting the second tissue section and a fastening side, positioned opposite said loop fastener tissue contacting side, with a plurality of loops;
   a suture being free of knots for engaging the first and second tissue sections to maintain the first and second tissue sections in a predetermined relationship;
   said plurality of hooks engaging said plurality of loops with a portion of said suture being held therebetween to sandwich and secure said suture relative to the first and second tissue; and
   an anchoring member for securing at least one of the hook and loop fasteners to tissue,
   wherein:
   the hook and loop fasteners are at least partially made of a biodegradable material;
   the plurality of hooks engage the plurality of loops to couple the first and second tissue sections;
   at least one of the hook and loop fasteners has an anchoring hole for receiving the anchoring member to thereby secure the at least one of the hook and loop fasteners to tissue, the anchoring member being made of a biodegradable material and selected from the group consisting of a staple, a rivet, and a suture; and
   at least a portion of one of the hook fastener tissue contacting portion and the loop fastener tissue contacting portion has a porous surface including a plurality of pores, each having a size of about 0.1 microns to 1000 microns, allowing soft tissue ingrowth to thereby secure the fastener to soft tissue.

2. The fastening system of claim 1 wherein at least a portion of the porous surface is a mesh structure having an array of substantially uniform spaces.

3. The fastening system of claim 1 wherein at least a portion of the hook fastener tissue contacting portion has a porous surface allowing tissue ingrowth to thereby secure the hook fastener to the first tissue section and at least a portion of the loop fastener tissue contact portion has a porous surface allowing tissue ingrowth to thereby secure the loop fastener to the second tissue section.

4. The fastening system of claim 1 wherein at least one of the hook and loop fasteners includes a therapeutic agent.

5. The fastening system of claim 1, wherein the porous surface has a series of randomly oriented fibers forming a series of pores having a range of sizes.

6. The fastening system of claim 1, wherein at least one of said hook fastener and loop fastener includes a therapeutic agent.

7. The fastening system of claim 6 wherein the therapeutic agent is selected from the group consisting of IGF (insulin-like growth factors), TGF (transforming growth factors), FGB (fibroblast growth factors), EGF (epidermal growth factors), BMP (bone morphogenic proteins), and PDGF (platelet-derived growth factors).

* * * * *